United States Patent [19]

Vesterager

[11] 4,324,256
[45] Apr. 13, 1982

[54] ELECTRODE DEVICE

[75] Inventor: Peter K. R. Vesterager, Maaløv, Denmark

[73] Assignee: Radiometer A/S, Copenhagen, Denmark

[21] Appl. No.: 20,870

[22] Filed: Mar. 15, 1979

[30] Foreign Application Priority Data

Mar. 28, 1978 [DK] Denmark .............................. 1361/78

[51] Int. Cl.³ .............................................. A61B 5/00
[52] U.S. Cl. ................................. 128/635; 204/195 B; 204/195 P
[58] Field of Search .............................. 128/635, 632; 204/195 B, 195 P

[56] References Cited

U.S. PATENT DOCUMENTS 3,664,178  5/1972  Spergel et al. .................. 128/635 X
3,795,239  3/1974  Eberhard ............................ 128/635
4,114,602  9/1978  Huch et al. ........................ 128/635

FOREIGN PATENT DOCUMENTS 2305049  8/1974  Fed. Rep. of Germany ...... 128/635

OTHER PUBLICATIONS

Vesterager, "Continuous Transcutaneous ... PO₂", *Measurement of Oxygen*, pp. 260-270, 1976.
Scacci et al., "O₂ Tension Monitoring", Medical Inst., vol. 10, No. 4, pp. 192-194, Jul., Aug. 1976.
Huch et al., "Transcutaneus PCO₂ ... ", The Lancet, May 7, 1977, pp. 982-983.

*Primary Examiner*—Lee S. Cohen
*Attorney, Agent, or Firm*—Hubbell, Cohen, Stiefel & Gross

[57] ABSTRACT

An electrode device for transcutaneous $PCO_2$ measurement with a pH-sensitive measuring electrode behind a $CO_2$-permeable membrane, a reference electrode, and an electrical heating device for thermostating the measuring electrode and thermally stimulating the blood flow in the skin in the measuring area, the reference electrode being in direct heat-conductive contact with the electrical heating device and being designed so that it surrounds the measuring electrode. This permits compact design of the electrode in a very small size.

7 Claims, 2 Drawing Figures

ELECTRODE DEVICE

The present invention relates to an electrode device for transcutaneous $PCO_2$ measurements.

The direct measurement of the partial pressure of carbon dioxide, $PCO_2$ by means of a $PCO_2$ electrode was first described in the literature by Stow and Randall (Am. J. Physiol. 179, 678, 1954 and Arch. Phys. Med. 38, 646, 1957).

The design of modern $PCO_2$ electrode devices is primarily based on the work by J. W. Severinghaus (Appl. Physiol. 13 515, 1958).

$PCO_2$ electrode devices comprise a $CO_2$-permeable membrane, behind which a pH-sensitive measuring electrode is arranged. The measuring area of the pH-sensitive measuring electrode is in contact with an electrolyte, the pH of which is a function of its $PCO_2$, in practice a bicarbonate solution, for example a sodium bicarbonate solution. The reference electrode, which is also in contact with the electrolyte, may be a calomel eletrode, or, if the electrolyte contains chloride, a silver chloride electrode.

The principle of the measurement is that the electrolyte between the $CO_2$-permeable membrane and the pH-sensitive glass electrode is equilibrated to a carbon dioxide concentration which is determined by Henry's law, and which is, hence, proportional to the partial pressure of carbon dioxide at the exterior of the membrane, and the pH measured by the glass electrode will depend on the ratio between carbon dioxide and bicarbonate in the electrolyte layer between the glass electrode and the membrane, so that the measured pH is a function of the $PCO_2$ in the measured sample at the exterior of the membrane. When the bicarbonate concentration in the electrolyte is selected in the correct range, that is, between $10^{-3}$ and $10^{-1}$ molar, the bicarbonate concentration may, for the present purpose, be considered constant, and under these conditions, the following relation applies (which corresponds to 100% sensitivity of the electrode):

log $PCO_2$ = constant-pH.

Suitable $CO_2$-permeable membrane materials are rubber and silicon rubber, both of which are especially permeable to carbon dioxide, but in recent years, especially Teflon ® membranes have been preferred for $PCO_2$ electrode devices. Teflon ® membranes are available in thicknesses down to 6 $\mu$m, and the carbon dioxide permeability of Teflon ® is satisfactory for the purpose.

$PCO_2$ electrode devices for measurements on blood samples are normally mounted in a thermostated measuring cell, and the complete measuring apparatus comprises a pH-meter, with extended scale in a sufficient interval around pH 6-8. For obtaining an accuracy better than 1% when measuring $PCO_2$ in blood samples, the temperature in the thermostated measuring cell must be regulated with an exactitude of less than 0.2° C., as the $PCO_2$ of the blood sample varies 4-6% per °C.

In recent years, $PCO_2$ electrode devices have been developed which measure a patient's blood $PCO_2$ transcutaneously and noninvasively, the $CO_2$-permeable membrane of the $PCO_2$-electrode device being applied against the patient's skin instead of being brought into contact with the blood sample.

In the electrode devices disclosed for this purpose, a thermostating to 37°-45° C. is performed, that is, a thermostating to above the normal skin temperature. This thermostating has a dual purpose, that is, partly to produce a local vasodilation and thereby local hyperemia for thermal stimulation of the blood flow in the skin in the measuring area, and partly, as explained above, to keep the electrode device at a well defined and exact measuring temperature to obtain exact $PCO_2$ measuring values.

A transcutaneous $PCO_2$ electrode device was described in 1960 (J. W. Severinghaus, Anesthesiology 21, 717, 1960).

In this work, Severinghaus discloses the use of a conventional $PCO_2$ electrode for transcutaneous measurement. The measuring electrode (the glass electrode) in the electrode device was surrounded by a jacket for a current of thermostating water, and the heat was transferred from the water jacket via the measuring electrode to the skin. In 1973, A. Huch et al. (Anaesthesist, 22, 379, 1973) described a heated $PCO_2$ electrode for transcutaneous $PCO_2$ measurement. The sensor electrode (the glass electrode) in the electrode device was surrounded by an electrically heated silver jacket, the reference electrode being unthermostated. The necessary heat for producing hyperemia in the skin in the measuring area was transferred directly from the silver jacket to the skin. In 1977 (The Lancet, 7th May, 982, 1977), this electrode was modified in such a way that the reference electrode (an Ag/AgCl-electrode) was also surrounded by the electrically heated silver jacket which delivered the necessary heat for producing local hyperemia in the skin in the measuring area. German published patent applications nos. 2,305,049 and 2,423,441 disclose transcutaneous $PCO_2$ electrode devices designed according to these principles.

Figure 1:
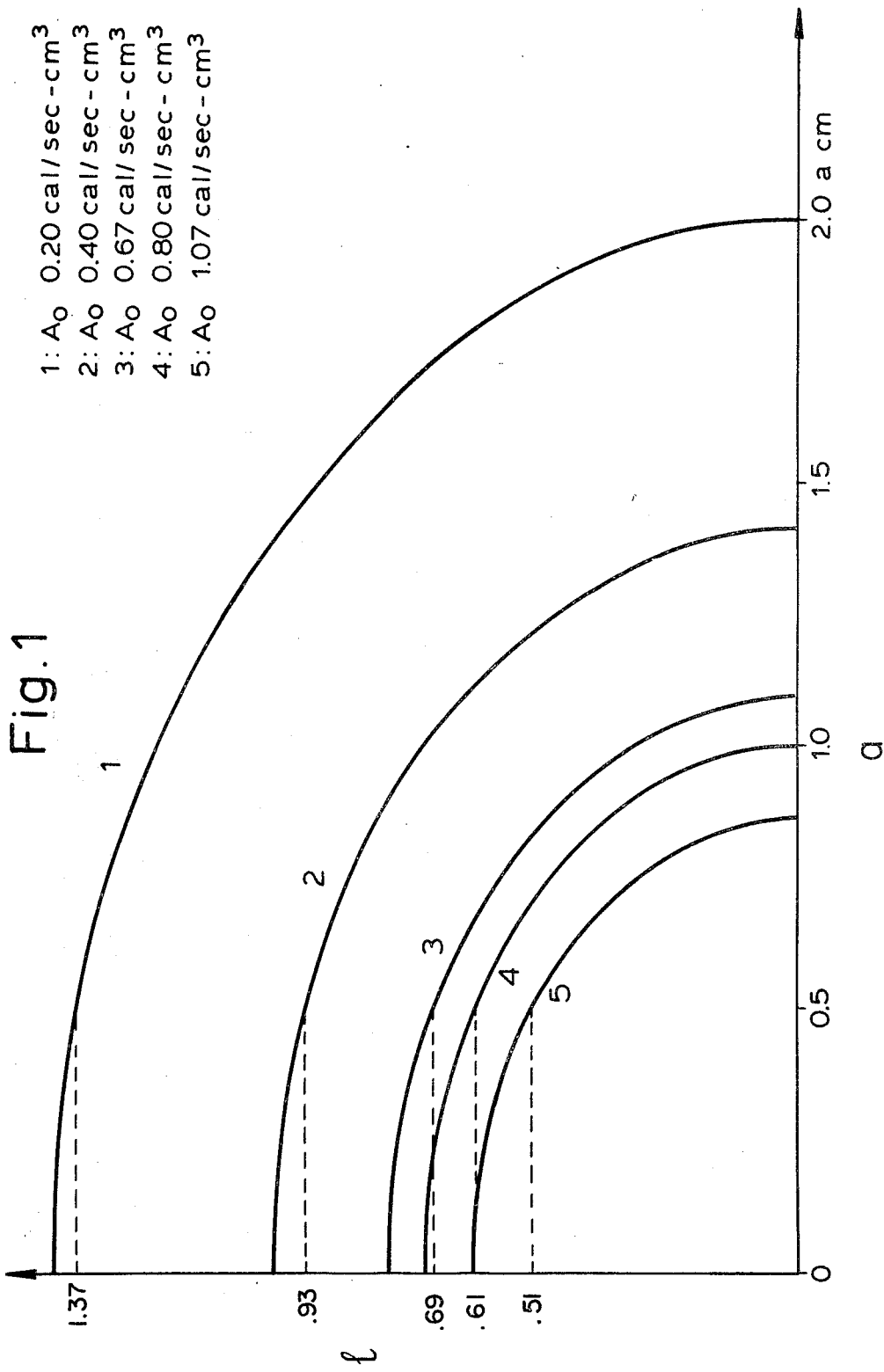
FIG. 1 is a plot of the length of the electrode versus the diameter for various heat supplies when the thermostating exactitude is 0.2° C.

The present invention provides a transcutaneous $PCO_2$ measuring electrode device having an improved and especially more compact design compared to the known transcutaneous $PCO_2$ electrode devices. Exactly the possibility of a compact design is of course of major importance in electrode devices which are to be applied on a patient's skin and to remain positioned there for a longer period, such as it is the case with transcutaneous $PCO_2$ electrode devices, especially in consideration of the fact that one patient group for which the transcutaneous $PCO_2$ measurement is specially important, are high risk neonates which may have a body weight as low as 1 kg.

The improved and more compact design is obtained by utilizing the reference electrode in the electrode device of the invention as the thermostating unit of the electrode and as means for transferring the heat necessary for thermal stimulation of the blood flow in the skin in the measured area, in addition to its function as reference electrode. Apart from the reduction of the number of necessary components for making the electrode, this results in the previously unattainable possibility of compact design of the electrode in a very small size.

Accordingly, the invention relates to an electrode device for transcutaneous $PCO_2$ measurement comprising a capsule suitable for application on a skin surface and having a $CO_2$ permeable membrane serving as contact face against the skin and a pH-sensitive measuring electrode arranged behind the membrane, the measuring area of the said electrode being in contact with an electrolyte positioned between the said measuring area and the membrane, a reference electrode communicating with the electrolyte, and a heating device for thermostating the measuring electrode and for thermal stimulation of the blood flow in the skin in the measured area, the reference electrode of the said electrode device being in direct heat-conductive contact with an electrical heating means and being shaped in such a way that it surrounds the measuring electrode and is in heat-conductive contact with the membrane for thermal stimulation of the local blood flow.

The reference electrode is preferably a silver/silver chloride electrode, in other words a silver body. On the one hand, this optimally fullfils the electrochemical requirements with respect to the function as a reference electrode, and on the other hand, this material is also excellent with respect to its properties as a heat conductor.

To obtain the most compact construction, which at the same time suitably fullfils the requirements to the necessary heat transport, it is preferred that the reference electrode be shaped as a hollow cylinder arranged concentrically around the measuring electrode.

Furthermore, in the most preferred design, the reference electrode is in direct heat-conductive contact with the measuring electrode for thermostating the measuring electrode.

It is preferred that the electrical heating device heating the reference electrode is a zener diode. A typical zener diode for use in the electrode device of the invention be a zener diode having a zener voltage of the order of 5-20 volts, for example about 12 volts. The advantage of using a zener diode is that when used as a heating device, the zener diode has a substantially current-independent voltage drop, which means that its power consumption can be monitored simply by means of an ammeter which is a much simpler equipment than a wattmeter. The monitoring of the power consumption of the zener diode may be utilized to obtain an indication of the blood flow in the skin in contact with the electrode device, as the heat consumption of the electrode device increases with increasing blood flow. It is generally known that in transcutaneous blood gas measurements, it may be of importance to simultaneously perform a monitoring of the blood flow in the measuring area. Another advantage of a zener diode is that it permits a simple and reliable regulation of the heating, for example by means of a suitable current generator. Finally, the zener diode has a suitable physical shape for being built into the electrode construction.

It is known to design electrode devices for transcutaneous oxygen partial pressure measurement with a measuring electrode surrounded by a reference electrode which concomitantly serves for thermostating and for transferring the necessary heat for thermal stimulation of the local blood flow in the measuring area. However, these known $PO_2$ electrode devices do not render the present invention obvious. Basic electrochemical differences between the $PO_2$ measurement and $PCO_2$ measurement constitute the reason why the skilled art worker would not consider to having the reference electrode take over the function of the heat conductor in $PCO_2$ electrode devices:

The $PO_2$ measurement is a polarographic measurement where the parameter measured as an expression of the $PO_2$ value of the measured object is an electrical current. In contradistinction to this, the $PCO_2$ measurement is a potentiometric measurement (a pH measurement) where the quantity measured is an electrical voltage. The size of this voltage, besides varying with the pH in the electrolyte, also varies to a considerable extent with the electrode temperature, including the temperature of the reference electrode. Therefore, from the outset it would be considered impossible that a reference electrode which were to deliver energy for the thermal stimulation of the blood flow in the skin could simultaneously be thermostated so exactly that its temperature could be kept within the exactitude necessitated by its function as a reference electrode, 0.2° C. Moreover, the development history of the transcutaneous $PCO_2$ electrode confirms that the possibility of obtaining this has not been taken into consideration. However, according to the invention it has been found that at a suitable shape of the reference electrode body, it is possible to obtain a thermostating exactitude of better than 0.2° C. with the heat input necessary for the thermal stimulation of the blood flow in the measuring area.

This has also been rendered probable theoretically, using as a model a cylinder having a radius a cm and a length 1 cm, and being directly heated (Conduction of Heat in Solids, 2d edition, Oxford 1959).

At "steady state", the temperature in the axial and radial directions is given by the following equations:

$$\frac{2K \cdot v_1}{A_o l^2} = 1 \text{ (axial direction)}$$

$$\frac{4K \cdot v_a}{A^o a^2} = 1 \text{ (radial direction)}$$

which gives $$v_1 = \frac{A_o l^2}{2K} \text{ and } v_a = \frac{A_o a^2}{4K}$$

To obtain a thermostating exactitude of better than 0.2° C. for the heat supply in question, the following equation must be fulfilled.

$$v_1 + v_a \leq 0.2° C.$$

When inserting the values for $v_1$ and $v_a$ the following expressions result:

$$\frac{l^2}{\frac{2K}{5A_o}} + \frac{a^2}{\frac{4K}{5A_o}} \leq 1$$

By inserting $A_o$ (that is, the heat supply which is necessary for producing vasodilation and for compensating for heat loss to the surroundings at the temperature in question), the equation may be solved, and solutions of the equation for various values of $A_o$ appear from FIG. 1. In the above equations, the symbols have the following meaning:

$A_o$: generation of heat, $$\frac{cal}{sec. \cdot cm^3}$$

a: radius of the cylinder, cm
K: thermal conductivity, $$\frac{cal}{cm \cdot sec \cdot °C}$$

l: length of the cylinder, cm
v: temperature, °C.
$v_1$: temperature in axial direction, °C.
$v_a$: temperature in radial direction, °C.

For example, the radius of the cylinder may be fixed at 0.5 cm, and one can then, from FIG. 1, read the maximum allowable length for a silver reference electrode for various values of $A_o$, when the requirement to thermostating exactitude is 0.2° C.:

| | | |
|---|---|---|
| For $A_o$: 0.2 | $\frac{cal}{sec \cdot cm^3}$ | l max = 1.37 cm |
| For $A_o$: 0.4 | — | l max = 0.93 cm |
| For $A_o$: 0.67 | — | l max = 0.69 cm |
| For $A_o$: 0.80 | — | l max = 0.61 cm |
| For $A_o$: 1.07 | — | l max = 0.51 cm |

It is noted that the above theoretical calculations merely prove that the necessary thermostating can in fact be obtained. In the particular actual cases, the conditions will usually (by building into an electrode capsule, etc.) be more favorable than presumed in the above calculations. Therefore, one can, in the particular case, possibly after initial calculations to obtain a guideline, adapt the design of the reference electrode in such a way that in its built-in condition, under the operation conditions of the electrode, it maintains a thermostating exactitude of 0.2° C. or better.

As the temperature sensor for use in the reference electrode, a thermistor is well suited.

The electrode device of the invention is applied on the patient's skin in such a way that the $CO_2$-permeable membrane is shielded from communication with the atmosphere, and the device is electrically connected to the measuring equipment adapted therefor. Such equipment comprises an amplifier and the desired conversion and registration units, together with a temperature registration and regulation unit (current supply unit) for the electrical hating and thermostating of the reference electrode. The electrode device of the invention may also be used in connection with an apparatus for continuous monitoring of a patient's blood pH of the type disclosed in Danish patent application No. 727/78.

Figure 2:
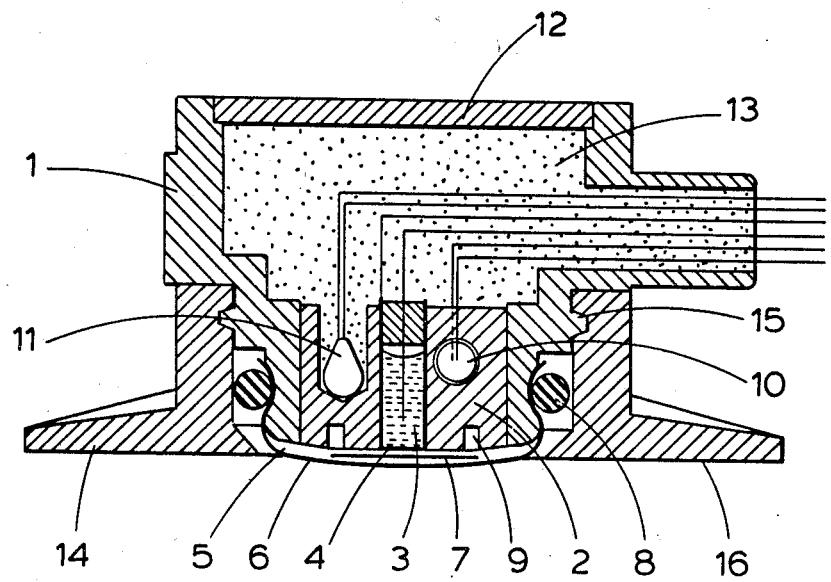
FIG. 2 is a vertical section of the electrode of the subject invention.

FIG. 2 shows an electrode device of the invention. In a housing 1 of electrically insulating material, for example ABS (acrylonitrile-butadiene-styrene), a reference electrode 2 is positioned. The reference electrode is a hollow cylindrical silver body. In the circular-cylindrical cavity of this body is positioned a measuring electrode 3 which is a pH measuring electrode, the measuring surface 4 of which is in contact with a sodium bicarbonate solution 5 which serves as an electrolyte and is positioned in an electrolyte space which is outwardly delimited by a Teflon ® membrane 6. Between the membrane and the surface of the pH measuring electrode is arranged a thin porous layer 7, for example of nylon web, cellophane, or Joseph paper, this layer being soaked with the bicarbonate solution. The membrane 6 is fixed by means of an O-ring 8. A cutting 9 in the silver body serves as an electrolyte reservoir. As an electrical heating device, a zener diode 10 is inserted in the silver body, and as temperature sensor is inserted a thermistor 11.

The capsule 1 is closed with a lid 12, and its interior cavity is filled with epoxy resin 13. A collar 14 in which the capsule 1 is fixed, for example screwed into the collar by means of a thread 15, comprises a contact face 16 which may be supplied with double face adhesive film for application of the electrode device against the skin and for eliminating contact between the atmosphere and the $CO_2$-permeable membrane. It is often preferred to apply a contact gel or a contact liquid between the $CO_2$-permeable membrane and the skin to obtain a better contact.

When the electrode device is used, the collar part 14 may suitably remain on the skin when the electrode device is to be calibrated, the electrode device then being screwed from the collar, calibrated and thereafter again screwed into the collar, possibly after application of a new contact gel or contact liquid.

The dimensions of the electrode device shown in FIG. 2 are suitably approximately as follows:

| | |
|---|---|
| Radius of the total electrode device minus the collar: | 0.8 cm |
| Height of the total electrode device: | 1.4 cm |
| Radius of the silver body 2: | 0.45 cm |
| Height of the silver body 2: | 0.7 cm |

I claim:

1. A potentiometric electrode device is transcutaneous $pCO_2$ measurement, said device comprising a capsule suited for application on a skin surface with a $CO_2$ premeable membrane closing one side of said capsule and serving as a contact face against the skin and a pH-sensitive measuring electrode located within said capsule, said electrode arranged behind the membrane, an electrolyte in contact with the measuring area of the said electrode and positioned between said measuring area and the membrane, a reference electrode communicating with the electrolyte, and a heating device in thermal communication with said measuring electrode for thermostating the measuring electrode and thermally stimulating the blood flow in the skin in the measured area, said heating device being capable of providing a heat level sufficient to produce vasodilation and for compensating for the heat loss to the surroundings, the reference electrode being in direct heat-conductive contact with the heating device, and the reference electrode surrounding the measuring electrode and being in heat-conductive contact with the membrane for thermal stimulation of the local bloodflow, said reference electrode having a predetermined shape capable of producing a thermostating exactitude of greater than 0.2° C. for said heat level.

2. An electrode device as claimed in claim 1, in which the reference electrode is a hollow cylinder arranged concentrically around the measuring electrode.

3. An electrode device as claimed in claim 1 or 2 in which the reference electrode is in direct heat-conductive contact with the measuring electrode for thermostating the measuring electrode.

4. An electrode device according to claim 3, in which the reference electrode is a silver/silver chloride electrode.

5. An electrode device according to claim 3, in which the heating device is a zener diode.

6. An electrode device according to claim 1 or 2, in which the reference electrode is a silver/silver chloride electrode.

7. An electrode device according to claim 1 or 2 in which the heating device is a zener diode.

* * * * *

UNITED STATES PATENT AND TRADEMARK OFFICE
CERTIFICATE OF CORRECTION

PATENT NO. : 4,324,256
DATED : Apr. 13, 1982
INVENTOR(S) : Peter K. R. Vesterager It is certified that error appears in the above—identified patent and that said Letters Patent is hereby corrected as shown below:

Col. 5, line 43: "hating" should read --heating--

Col. 6, line 27: "is" should read --for--

Signed and Sealed this

Thirty-first Day of July 1984

[SEAL]

Attest:

GERALD J. MOSSINGHOFF

Attesting Officer          Commissioner of Patents and Trademarks